United States Patent
Fumo

(10) Patent No.: US 11,602,452 B2
(45) Date of Patent: Mar. 14, 2023

(54) METHOD AND DEVICE FOR RESTRAINING A HUMAN BODY

(71) Applicant: Nelson Fumo, Tyler, TX (US)

(72) Inventor: Nelson Fumo, Tyler, TX (US)

( * ) Notice: Subject to any disclaimer, the term of this patent is extended or adjusted under 35 U.S.C. 154(b) by 107 days.

(21) Appl. No.: 16/928,152

(22) Filed: Jul. 14, 2020

(65) Prior Publication Data

US 2021/0315725 A1    Oct. 14, 2021

Related U.S. Application Data

(60) Provisional application No. 63/008,703, filed on Apr. 11, 2020.

(51) Int. Cl.
*A61F 5/00*      (2006.01)
*A61F 5/37*      (2006.01)
*A47D 15/00*    (2006.01)

(52) U.S. Cl.
CPC .......... *A61F 5/3784* (2013.01); *A47D 15/008* (2013.01)

(58) Field of Classification Search
CPC ................. A47D 15/008; A61F 5/3784; A61F 5/3769; A61F 5/37
See application file for complete search history.

(56) References Cited

U.S. PATENT DOCUMENTS

| | | | | |
|---|---|---|---|---|
| 2,014,478 | A | * | 9/1935 | Luetteke ............... A47D 15/008 24/72.5 |
| 2,553,007 | A | * | 5/1951 | Rosenthal ............ A47D 15/008 5/424 |
| 4,471,767 | A | * | 9/1984 | Guimond ............... A47D 13/08 601/24 |
| 6,192,835 | B1 | * | 2/2001 | Calhoun ............... A01K 27/003 119/792 |
| 2013/0036551 | A1 | * | 2/2013 | McGann ............... A61F 5/3784 5/621 |
| 2013/0092088 | A1 | * | 4/2013 | Sharp ....................... A01K 5/01 119/61.5 |
| 2019/0191858 | A1 | * | 6/2019 | Wagner ..................... A45F 5/00 |

* cited by examiner

*Primary Examiner* — Steven O Douglas

(57) ABSTRACT

A method and device for limiting the displacement of a human body without restricting natural movements are disclosed. The device is an anchor that is anchored to a bedsheet. The method describes the use of the anchor with a connecting element such as a ribbon. One end of the connecting element is attached to the anchor and the other end to a garment or harness at the perineal region of a human body. The main application of the method and device is to keep a child in a bed without the risk of falling out of bed, but applies to any person, lying down or sitting, regardless of age.

2 Claims, 1 Drawing Sheet

METHOD AND DEVICE FOR RESTRAINING A HUMAN BODY

FIELD OF THE INVENTION

The present invention pertains to devices like safety belts or body harnesses and methods for limiting the displacement of the human body.

BACKGROUND

For any child that has not learned how to sleep without falling out of a bed, as for toddlers transitioning from a crib to a bed, accidents are common. A little one not accustomed to the freedoms of a bigger bed might have trouble learning how to not to roll out of the bed and onto the floor. The present invention, as a safety method and device, is a simple solution to keep a child in bed without the risk of falling out of a bed.
For an adult with physical or mental limitations, or just for sleepwalkers, the method and device of the present invention can avoid the adult to get or fall out of the bed.

SUMMARY

The method and device of the present invention overcome some or all the shortcomings of existing complicated and bulky prior arts used to restrain a child in a bed. Although the present invention was conceived for a child in a bed, in general, the method and device of the present invention apply to any person, regardless of age.

The device of the present invention is an anchor named 'bedsheet double-cap mechanical anchor' comprised of two caps, the 'top cap' and the 'bottom cap,' which are locked together while holding a bedsheet in between.

The method uses the 'bedsheet double-cap mechanical anchor' to restrain a person by using a connecting element such as a ribbon. One end of the connecting element is attached to the anchor and the other end is attached to a garment at the perineal region of the person. The use of the perineal region facilitates natural movements of arms and legs, while limiting the displacement based on the position of the anchor and the length of the connecting element.

DETAILED DESCRIPTION OF PREFERRED EMBODIMENT

The description refers to restraining a child that could fall out of a bed but is not intended to limit the scope of the invention in any way.

Figure 1:
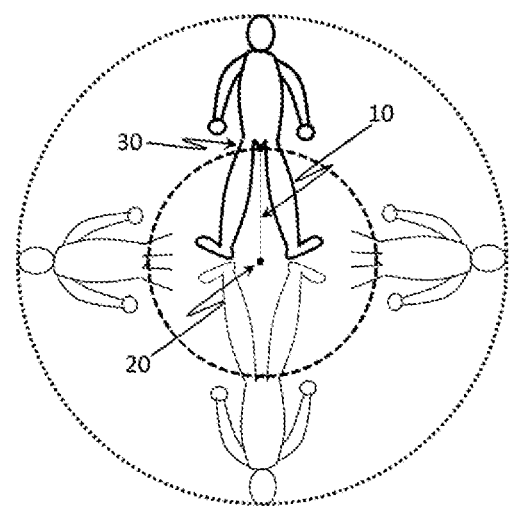
FIG. 1 shows the range of mobility of a child lying on a bed when the device and method of the present invention are used. One end of the connecting element 10 is attached to the bedsheet double-cap mechanical anchor 20 and the other end of the connecting element 10 is attached to a garment or harness at the perineal region 30 of the child.

FIG. 1 illustrates how the anchor 20 limits the displacement of the child when lying on a bed based on the length of the connecting element 10 attached to a garment or harness at the perineal region 30 of the child. The child will be able to move freely his/her legs and arms but within the limitations imposed by the position of the anchor 20 and the length of the connecting element 10 as shown in the figure.

Figure 2A:
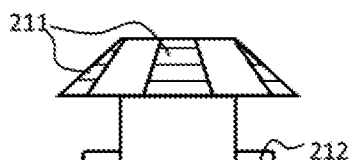
FIG. 2A shows the side view of the top cap 210 of the bedsheet double-cap mechanical anchor 20.
Figure 2C:
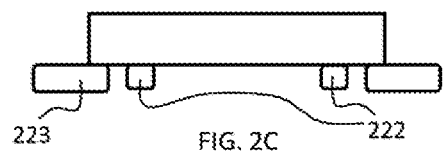
FIG. 2C shows the side view of the bottom cap 220 of the bedsheet double-cap mechanical anchor 20.
Figure 2B:
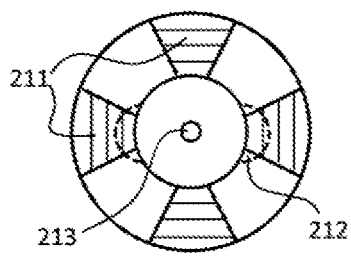
FIG. 2B shows the top view of the top cap 210 of the bedsheet double-cap mechanical anchor 20.

The device of the present invention, the anchor 20, named bedsheet double-cap mechanical anchor, is shown in FIGS. 2A and 2B. The embodiment comprises a top cap 210 and a bottom cap 220.

Figure 2D:
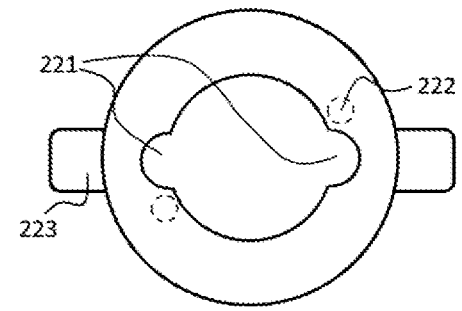
FIG. 2D shows the top view of the bottom cap 220 of the bedsheet double-cap mechanical anchor 20.

The locking mechanism, to lock both top and bottom caps, has a gap between them such that when they are locked, allows both caps to be physically separated by a bedsheet without damaging it. FIG. 2A is the side view of the top cap 210 where the indents 211 represent any kind of engrave or texture on the exterior surface of the cap to facilitate its grip and rotation. The fins 212 are part of the locking mechanism. FIG. 2B is the top view of the top cap 210 illustrating a hole 213 as a means of attaching the connecting element, such as a ribbon, to the cap. FIG. 2C is the side view of the bottom cap 220, where the pins 222 are used to stop the rotation of the top cap 210 when both caps are locked, this happens when the fins 212 reach the pins 222. FIG. 2D is the top view of the bottom cap 220. The two notches 221 are part of the locking mechanism through which the fins 212 pass through the bottom cap 220. The protruding shapes 223 are optional and used to help to hold the bottom cap 220 while the top cap 210 is inserted through it and rotated to lock the two caps.

Figure 3A:
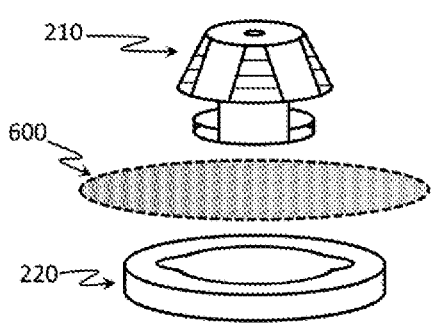
FIG. 3A shows how the bottom cap 220 of the bedsheet double-cap mechanical anchor 20 is placed underneath a bedsheet 600 and the top cap 210 of the bedsheet double-cap mechanical anchor 20 is placed above the bedsheet 600 before both caps are assembled.
Figure 3B:
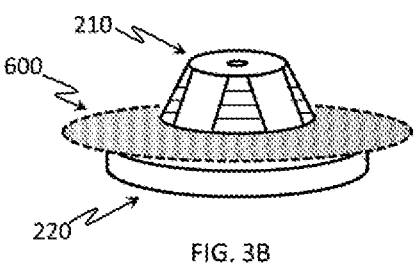
FIG. 3B illustrates the assembling of the top cap 210 and the bottom cap 220 of the bedsheet double-cap mechanical anchor 20 to a bedsheet 600.

FIGS. 3A and 3B shows how the anchor 20, named bedsheet double-cap mechanical anchor, is installed. FIG. 3A shows how the bedsheet double-cap mechanical anchor 20 is assembled to be attached to a bedsheet 600. The bottom cap 220 is placed underneath the bedsheet 600, the fins 212 of the top cap 210 are aligned with the notches 221 in the bottom cap 220 and pushed against the bedsheet 600 to reach the bottom, the top cap 210 is rotated to lock the two caps having the bedsheet 600 in between. FIG. 3B illustrates the top cap 210 on top of the bedsheet 600 and the bottom cap 220 underneath the bedsheet 600 after these two caps of the bedsheet double-cap mechanical anchor have been assembled or attached to the bedsheet 600.

Operation of the Presently Preferred Embodiment

To restrain a child from falling out of a bed, a point in the bed is identified. This point must be far from any edge of the bed a maximum distance equal to the length of the connecting element (such as a ribbon) plus the length from the child's head to the perineal region where the other end of the connecting element will be attached. This distance will ensure the child's head will always be inside the perimeter of the bed. The reference maximum length of the connecting element cannot be longer than the distance from the perineal region of the child to the child's neck to avoid any possibility that the connecting element gets around the child's neck. The perineal region is selected for the method because it allows the child to move arms and legs freely within the restricted area imposed by the present invention.

Once the point on the bed has been identified, and with reference to FIG. 2A, 2B, 3A and FIG. 3B, the bottom cap 220 of the bedsheet double-cap mechanical anchor is placed at this point but underneath the bedsheet 600. The top cap 210 is placed on top of the bedsheet aligning the fins 212 of the top cap 210 with the notches 221 of the bottom cap 220. Once the caps have been aligned, the top cap 220 is pushed against the bedsheet 600 to go through the bottom cap 220. Pressing the top cap 210 against the bedsheet 600 and bottom cap 220, the top cap 210 is rotated until reaches the stop pins 222 on the bottom cap 220. After both caps have been locked having the bedsheet in between, the connecting element, such as a ribbon, attached to the top cap 210 is pulled strongly in all directions to make sure the bedsheet double-cap mechanical anchor has been firmly anchored to the bedsheet 600.

In reference to FIG. 1, once the bedsheet double-cap mechanical anchor 20 has been fixed to the bedsheet 600, the connecting element 10 can be attached by any means to a garment or harness at the perineal region 30 of the child.

What is claimed is:

1. An bedsheet double-cap mechanical anchor, for restraining a human body to a bed, the bedsheet double-cap mechanical anchor comprising:
  a top cap,
    wherein the top cap is half of a locking mechanism locking mechanism that is used to lock the top cap to a bottom cap having a bedsheet disposed therebetween,
    wherein there is a point of connection at the top cap where one end of a connecting element including a ribbon is attached to the anchor at one end and another end of the connecting element is connected to a garment or harness adapted to be attached to a human body,
    wherein a surface of the top cap is engraved to facilitate gripping for rotation and locking with the bottom cap,
    wherein the bottom cap is the remaining half of the locking mechanism that is used to lock the top cap to the bottom cap having the bedsheet in between.

2. A method for restraining a human body using the bedsheet double-cap mechanical anchor of claim 1, in which the bedsheet double-cap mechanical anchor is anchored to a fitted sheet in a bed.

\* \* \* \* \*